(12) United States Patent
Suddaby

(10) Patent No.: US 6,395,034 B1
(45) Date of Patent: May 28, 2002

(54) INTERVERTEBRAL DISC PROSTHESIS

(76) Inventor: Loubert Suddaby, 76 Tanglewood Dr., Orchard Park, NY (US) 14127

( * ) Notice: Subject to any disclaimer, the term of this patent is extended or adjusted under 35 U.S.C. 154(b) by 0 days.

(21) Appl. No.: 09/448,490

(22) Filed: Nov. 24, 1999

(51) Int. Cl.[7] ................................................. A61F 2/44
(52) U.S. Cl. ................................ 623/17.15; 623/17.12
(58) Field of Search ......................... 623/17.11, 17.12, 623/17.13, 17.14, 17.15, 17.16

(56) References Cited

U.S. PATENT DOCUMENTS

| | | | | |
|---|---|---|---|---|
| 4,404,327 A | * | 9/1983 | Crugnola | 523/228 |
| 4,722,948 A | * | 2/1988 | Sanderson | 523/115 |
| 5,458,641 A | * | 10/1995 | Ramirez Jinenez | 623/17.11 |
| 5,571,189 A | * | 11/1996 | Kuslich | 623/17.11 |
| 5,916,267 A | * | 6/1999 | Tienboon | 623/17.11 |
| 6,146,422 A | * | 11/2000 | Lawson | 623/17.11 |
| 6,159,244 A | * | 12/2000 | Suddaby | 623/17.11 |
| 6,174,334 B1 | * | 1/2001 | Suddaby | 623/17.11 |
| 6,176,881 B1 | * | 1/2001 | Schar | 623/17.11 |
| 6,183,518 B1 | * | 2/2001 | Ross | 623/17.16 |
| 6,231,615 B1 | * | 5/2001 | Preissman | 623/23.73 |

* cited by examiner

Primary Examiner—Bruce Snow
(74) Attorney, Agent, or Firm—Shoemaker and Mattare

(57) ABSTRACT

An intervertebral disc is replaced with a construct including an expandable stent having convex heads and a hardenable material, such as a resin, which is injected into the intervertebral space around the stent and allowed to harden in situ.

9 Claims, 7 Drawing Sheets

INTERVERTEBRAL DISC PROSTHESIS

BACKGROUND OF THE INVENTION

This invention relates to orthopedic surgery, more particularly to a prosthetic intervertebral disc, and stent used in the construction thereof, and a surgical procedure for implanting the construct in the intervertebral disc space.

The normal intervertebral disc has an outer fibrous ring, constituted mainly of collagen fibers, which strongly binds the vertebral elements together. This fibrous outer layer, or annulus, encircles a soft gel-like matrix, or nucleus, which serves both as a cushion and as a mobile and compressible element that allows motion to occur between the vertebral bodies above and below the intervertebral disc. This gel matrix is 95% water. The types of motion that can occur at the level of the intervertebral disc include flexion, extension, lateral bending and varying degrees of torsion or rotation.

In the course of a day, the normal intervertebral disc may encounter various combinations of these bending or twisting motions several thousand times. As a consequence of such repetitive motion, natural discs deteriorate over time, much as the padded cushion on a well-used chair might do.

The effect of this deterioration is a loss of water content of the gel matrix of the nucleus and a concomitant compacting of its fibers with a resultant loss of disc space height which in turn causes a loosening of the surrounding support ligaments of the spine and the development of what is termed degenerative instability. This instability results in a pathologic excess of movement at the intervertebral disc space that further accentuates the degeneration of both the nucleus and the annulus of the disc. With continued deterioration, the annulus of the disc can bulge or even develop radial tears that allow the inner nuclear material to protrude or even extrude from the disc space. This bulging of the annulus or protrusion of the nucleus can compress nerves and cause disabling sciatic pain. Distension or bulging of the annulus alone is frequently sufficient to produce disabling back pain because or compression or inflammation of free nerve endings present in the outer annulus of the disc.

The time-honored method of addressing degenerative lumbar instability resulting from severely damaged intervertebral discs has been to remove the damaged disc and fuse the two adjacent vertebral bones to eliminate pathological motion. While this approach does well at eliminating pathological motion, it also prevents any natural motion at that segment. The consequence of eliminating natural motion at a single segment generally is that greater degrees of stress occur above or below that segment. This in turn accelerates degeneration of the neighboring intervertebral spaces, often necessitating additional fusion surgeries.

It would be desirable, therefore, to preserve natural motion at every disc space and thus eliminate the degenerative domino effect that disectomy and fusion seems to produce. Since the earliest pathologic change evident in a degenerative disc is loss of water content with conco-mitant loss of disc space height, maintenance of disc space height seems critical for maintaining the way opposing vertebral surfaces alter position with each other during bending and twisting. Indeed, loss of disc space height seems to be the most crucial early feature of degenerative instability. With degenerative instability the ligaments may ultimately become so lax that buckling of the ligaments occurs, or even pathologic slippage of the spine (spondylolithesis). Preserving disc space height is therefore important in preventing secondary degenerative changes that occur as a consequence of loss of disc space height from mechanical damage or dessication due to aging.

An intervertebral disc endoprosthesis ought, ideally, to restore and preserve disc space height while permitting sufficient natural motion (flexion, extension, lateral bending, and rotation) to prevent excessive stresses on spinal segments above and below the prosthesis. Natural motion may also play a role in the health of the annulus and surrounding ligaments, much as natural stresses play a role in the maintenance of strength and density of normal living bone.

Many synthetic structures have been used as intervertebral disc implants, but few materials are durable enough to withstand the tremendous and repetitive forces a natural disc must withstand. In addition, the majority of intervertebral implants fail to restore and maintain sufficient disc space height to keep spinal support ligaments taut. Many constructs designed to address natural motion at the disc space have either been to complex to achieve commercial success or too challenging to implant, from a surgical perspective.

SUMMARY OF THE INVENTION

It is an object of this invention to provide an intervertebral disc endoprosthesis that simultaneously restores sufficient disc space height and mobility to provide a semblance of functional normalcy and to reduce or eliminate abnormal stresses on adjacent intervertebral segments.

Another object is to provide an intervertebral disc endoprosthesis which is simple to implant surgically and easy to manufacture from common materials.

To achieve these objectives, a stent according to this invention includes at least two telescoping elements, each having a head adapted to engage an endplate of each of the adjacent vertebral bodies, and means for changing the distance between said heads.

The stent is placed between adjacent vertebral bodies in a collapsed state, after the nucleus of the disc has been removed, through a small disectomy incision. The stent is then expanded in the disc space until the paraspinal ligaments and annular structures are taut and disc space height is restored. The end surfaces of the stent contacting the vertebral body endplate is smooth and convex, mirroring the normally concave surface of the vertebral endplate. The convex surfaces are in turn held apart by a connecting rod that allows expansion but not contraction when in use. The convex surface also has a spike or spur that digs into the endplate in its center portion to resist movement or shifting of the stent during distraction. This spike or spur also serves to prevent extrusion of the construct assembly in its final state. Once satisfactory distraction of the disc space has occurred, and the annulus and surrounding ligaments are deemed to be taut, the empty space formerly occupied by the damaged nucleus is replaced by synthetic material such as a resinous polymer or plastic that conforms to the shape of the nuclear envelope formed by the annulus and surrounding support ligaments. As the resin polymerizes, it hardens to form a stable endoprosthetic construct having a superior and inferior smooth metallic surface in contact with the vertebral endplates, and a surrounding ring of resinous material, that serves both to stabilize the stent and to replicate the gross anatomy of the enucleated segment of the disc. This construct serves to restore disc space height and annular ligamentous tension while simultaneously allowing the duplication of natural motion by virtue of its anatomic conformity to the preexisting disc nucleus.

The stent may be made of titanium or steel, or any other readily available biocompatible material already in use for human implantation. Any of currently available bone cements may be used for the polymer component of the construct, because they have been demonstrated to be biocompatible and have been used extensively in orthopedic joint implants. Bone cement is ideally suited as an endoprosthesis for disc replacement because it exhibits far greater strengths under compressive loads than under tensile forces. The forces which normally act on an intervertebral endoprosthesis are compressive in nature. Alternatively, any of a variety of synthetic materials that can be injected in a liquid or semisolid form and then allowed to harden could be used. Acrylics and carbonates, or other plastic materials, might also be used.

Because the endoprosthesis is in effect assembled within the disc space, the size of the stent in its collapsed state and its convex endplate surfaces are the only limiting factor regarding the size of the disectomy needed to allow implantation of the endoprosthesis, since bone cement or other synthetic polymers or plastics can be injected through relatively small ports. This potentially allows for endoprosthesis implantation through endoscopic or other similar minimally invasive surgical techniques. Indeed, because of the minimal exposure necessary for insertion of such a component construct, surgical implantation in an outpatient setting should be technically feasible. In addition, multiple disc replacements in a single sitting may be possible because of the ease of implantation.

Disc replacements done according to this invention would seem best suited to early disc degenerative conditions or so-call "black discs", where the envelope of annular and longitudinal support ligaments are largely intact. A simple endoprosthesis in this setting can serve either as a permanent disc replacement, or as a means of temporizing and preserving functional mobility for the longest period of time possible prior to surgical fusion of the damaged segment.

BRIEF DESCRIPTION OF THE DRAWINGS

In the accompanying drawings,

FIG. 1A shows a ratchet-type intervertebral stent, in its collapsed condition, while

DESCRIPTION OF THE PREFERRED EMBODIMENT(S)

FIGS. 1A, 1B, 2A and 2B show two forms of an intervertebral stent according to this invention, the only difference being the mechanism provided for expanding the stent. Each stent comprises a pair of elements 10,12, each having a broad head 14 with a convex surface 16 facing outwardly, away from the other element. By "convex", I mean rounded, generally. A head whose surface is partially spherical is presently preferred. In any event, the geometry of the head (i.e., its radius of curvature) should be chosen to match that of the vertebral endplate against which it will bear. Those vertebral endplate surfaces are normally concave.

Figure 1A:
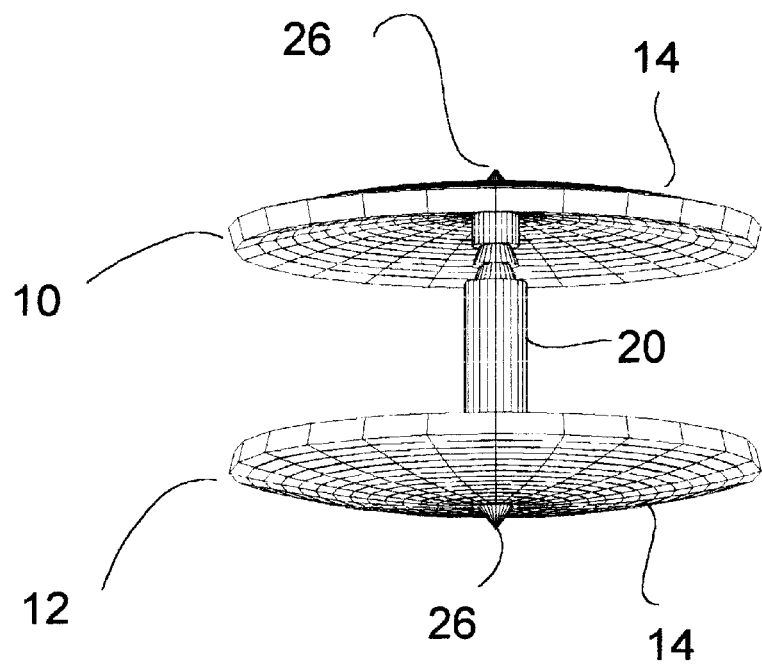
Figure 1B:
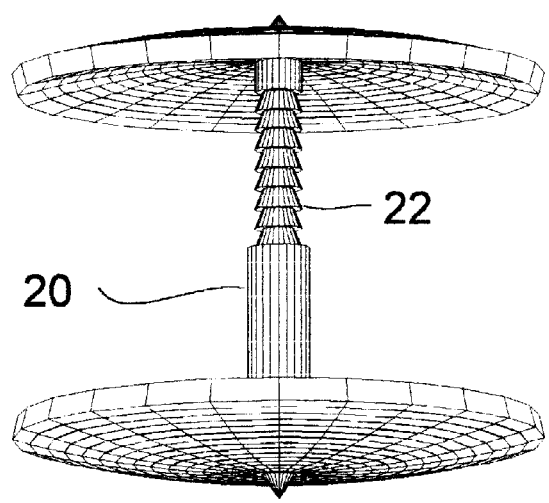
FIG. 1B shows the stent in its expanded condition.
Figure 2A:
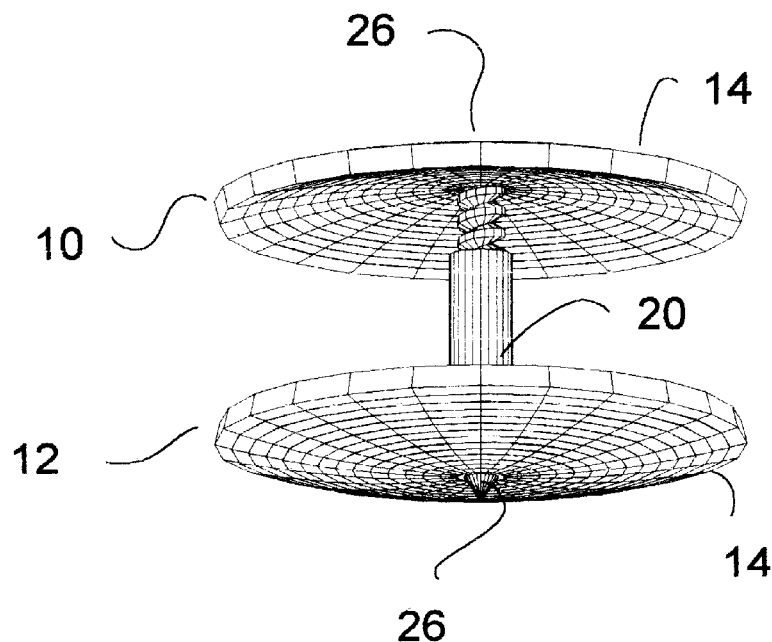
FIG. 2A shows a screw-type intervertebral stent in its collapsed condition.
Figure 2B:
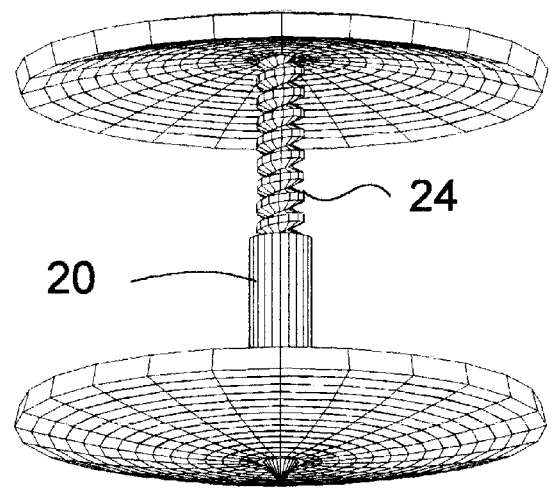
FIG. 2B shows the stent in its expanded condition.
Figure 3A:
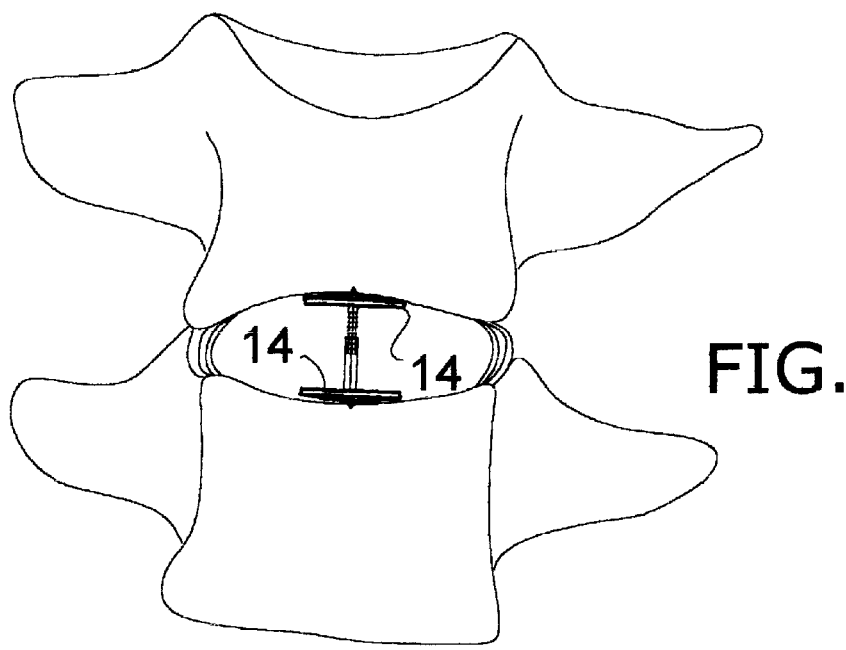
FIG. 3A is an anterior view of a segment of a spine, showing the stent of FIG. 1, collapsed and positioned between vertebral bodies.
Figure 3B:
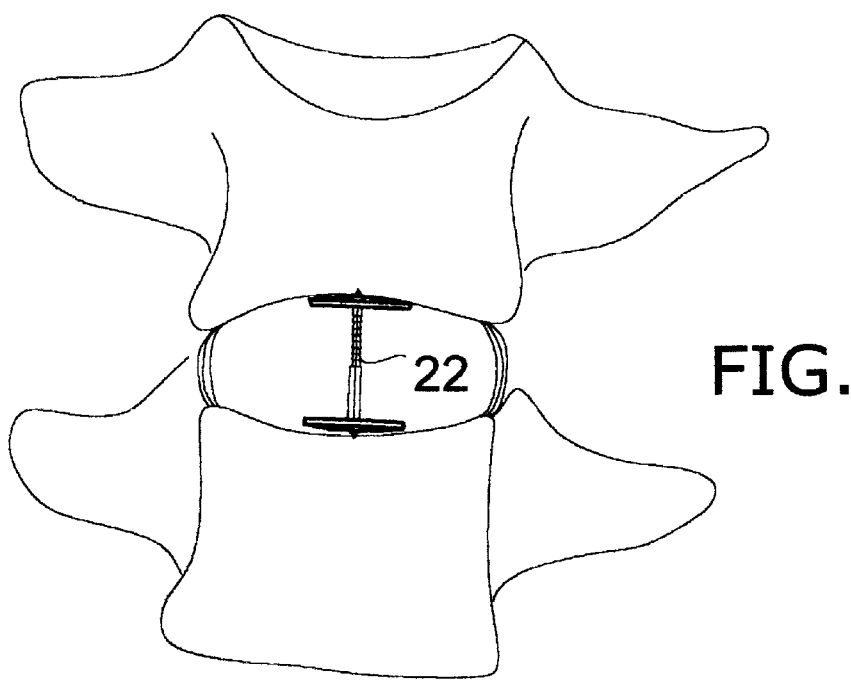
FIG. 3B shows the stent expanded.
Figure 4A:
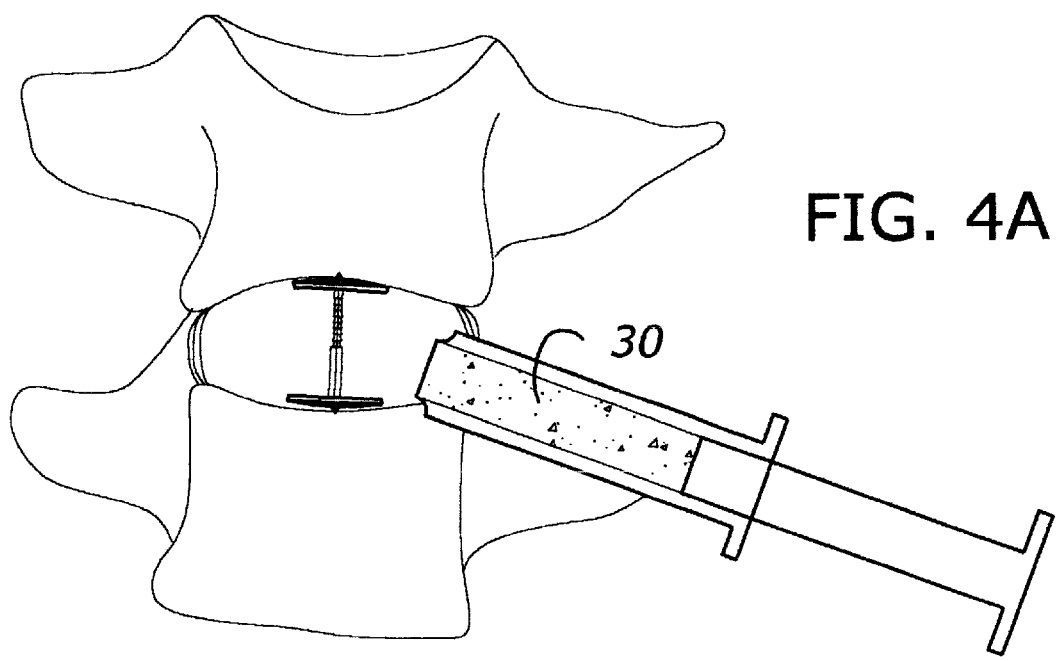
FIGS. 4A and 4B are similar to FIG. 3B, showing two stages of injection of a hardenable material.
Figure 4B:
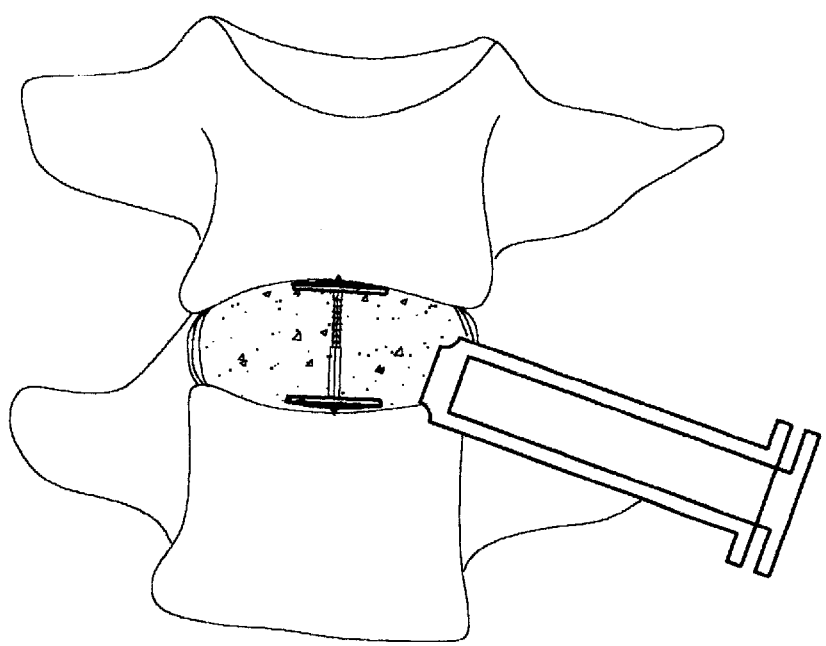
Figure 5A:
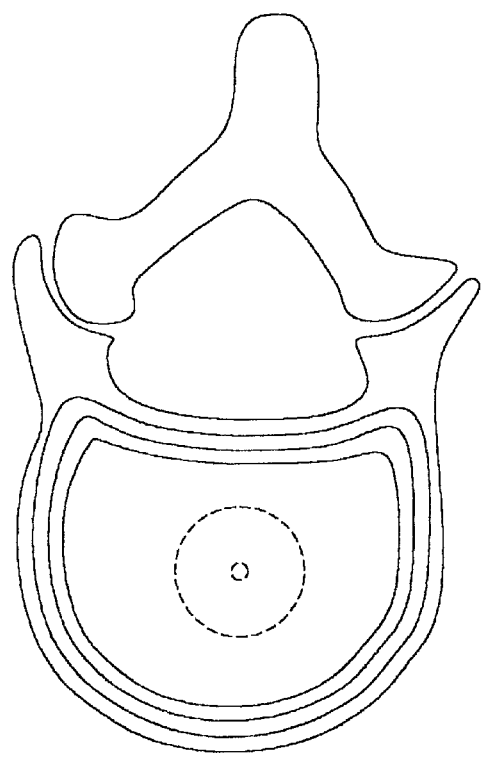
FIGS. 5A and 5B are cranial-caudal (top) views taken on the section line 5A—5A and 5B—5B in FIGS. 4A and 4B, respectively.
Figure 5B:
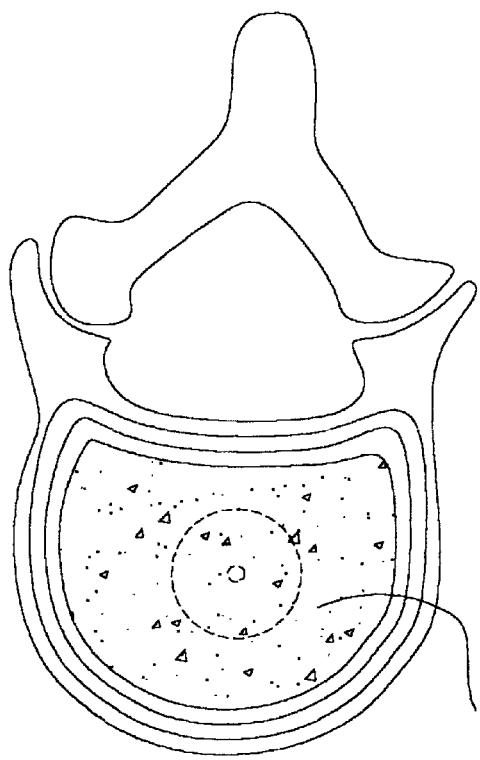
Figure 6A:
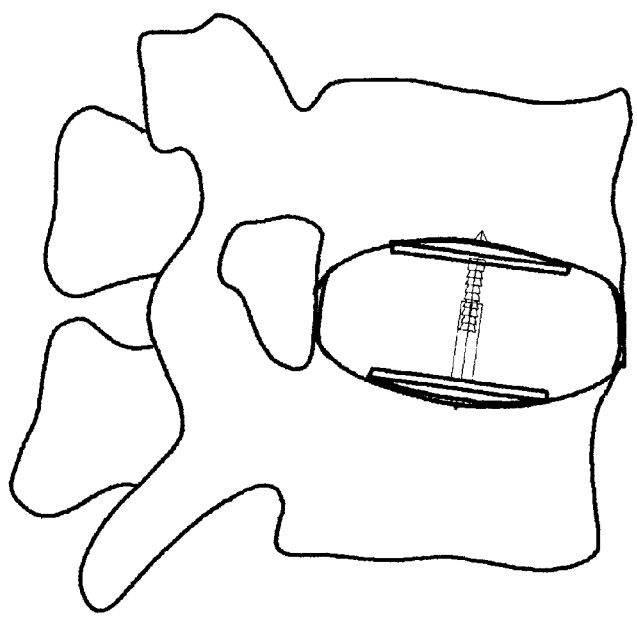
FIGS. 6A and 6B are lateral (side) views showing a stent in its contracted and expanded configurations, respectively.
Figure 6B:
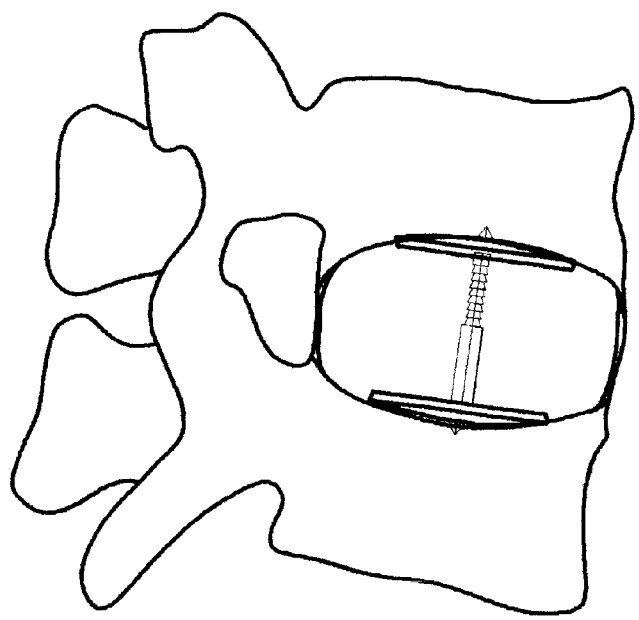
Figure 7A:
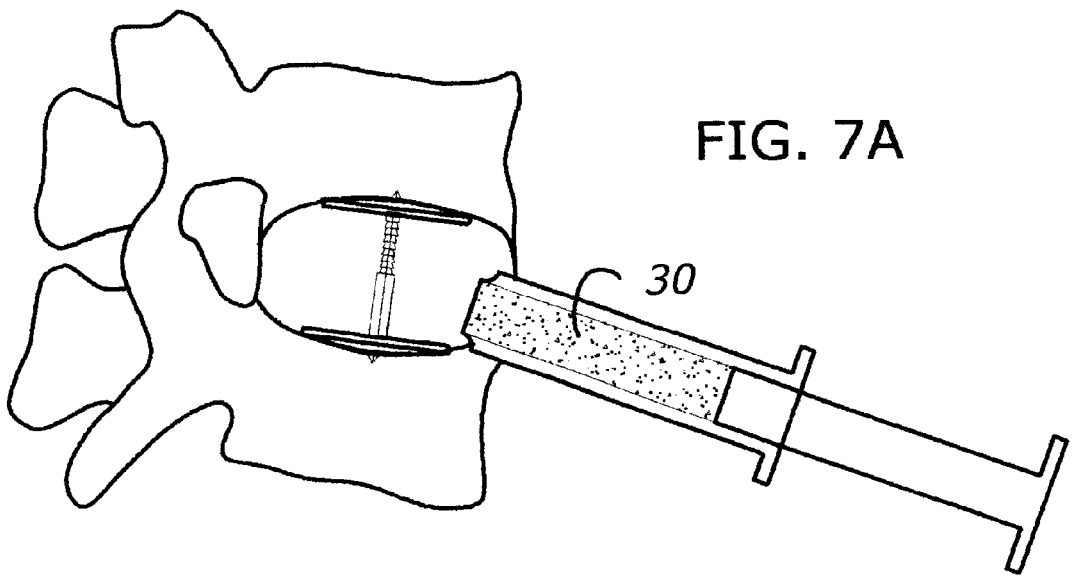
FIGS. 7A and 7B are lateral views showing the injection of hardenable material around the stent.
Figure 7B:
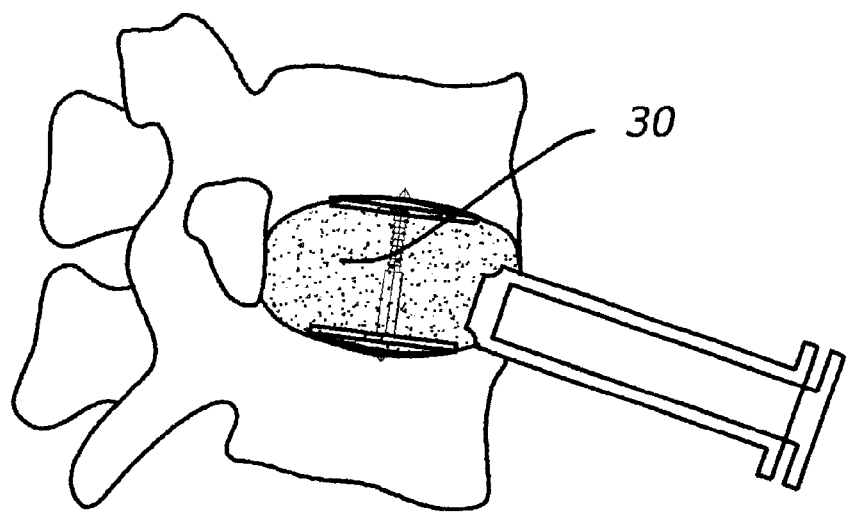

A telescoping mechanism extends between the heads, so that they can be retracted and distracted, that is, driven toward or away from one another. In either of the two contemplated mechanisms (FIGS. 1 and 2, respectively), each head has a stem 20, and the two stems have structure which allows them to be moved lengthwise, but prevents unintended retraction. In FIGS. 1A and 1B, that mechanism includes opposed ratchet teeth 22 which permit only outward movement; in FIGS. 2A and 2B, the mechanism is a screw mechanism 24 which requires relative turning of the parts.

Each head of the stent has at least one spur or small spike 26 extending from it, to dig into the facing vertebral endplate, so as to resist lateral dislodgement of the stent after placement.

The endoprosthesis of this invention includes both the stent described above and a mass of material 30 which is hardened in situ around the stent, in the disc space. This material is one which may be injected into the disc space around the stent, most preferably a setting resin.

In use, the surgeon first makes a small incision, through which he removes the damaged disc from its intervertebral space. He then inserts a stent, in its collapsed configuration, through the incision. After placing the stent so its heads face the endplates of the vertebral bodies in the correct position, he manipulates the telescoping mechanism to drive the heads apart until he judges that the intervertebral space is at is desired natural height. By now the stent is under compression from the paraspinal ligaments, and the spurs at either end dig into the endplates to prevent the stent from moving laterally. Now, the selected hardenable material is injected through the incision, into the disc space, completely filling it and enveloping the stent. Once the material has hardened, the stent is permanently embedded in it, and its convex end plates provide bearing points that permit natural relative movement of the vertebral bodies on either side.

It should be understood that because this invention is subject to variations and modifications, the foregoing description and the drawings should be interpreted as only illustrative of the invention described by the following claims.

I claim:

1. A method of replacing a damaged intervertebral disc, comprising steps of removing a damaged disc nucleus from its intervertebral space, inserting an expandable stent having opposed convex heads and structure extending between the heads which is expandable lengthwise, but not retractable, into the intervertebral space, placing the stent so that its convex ends face the endplates of the respective vertebral bodies on either side of the intervertebral space, expanding said structure so that the heads bear against the endplates, injecting a hardenable material into the intervertebral space between the convex heads, and allowing the hardenable material to harden around the stent so as to form a permanent disc prosthesis.

2. The method of claim 1, wherein the stent has points on each of said convex ends, and the expanding step includes pressing the points against the endplates of the respective vertebral bodies on either side of the intervertebral space.

3. An intervertebral disc prosthesis, comprising a stent having at least two telescoping elements, each of said elements having a head adapted to engage an endplate of a respective one of said vertebral bodies, a structure extending between said heads, said structure be expandable lengthwise, but not retractable, and a mass of hardenable material for filling the space between said heads.

4. The stent of claim 3, wherein each of said heads has a convex surface for engaging the endplate of a respective one of said vertebral bodies.

5. The stent of claim 3, wherein each of said heads has a point for digging into the endplate of a respective one of said vertebral bodies, to keep the stent in place.

6. The prosthesis of claim 3, wherein each of said heads has a convex surface for engaging the endplate of a respective one of said vertebral bodies.

7. The prosthesis of claim 3, wherein each of said heads has a point for digging into the endplate of a respective one of said vertebral bodies, to keep the stent in place.

8. The prosthesis of claim 3, wherein said hardenable material is a plastic polymeric material.

9. The prosthesis of claim 8, wherein said material is a resin.

* * * * *